United States Patent
Lee et al.

(10) Patent No.: US 8,031,884 B2
(45) Date of Patent: Oct. 4, 2011

(54) METHOD AND APPARATUS FOR REPRODUCING MUSIC FILE

(75) Inventors: Sun-Gi Lee, Seoul (KR); Kang-Hoon Lee, Yongin-si (KR); Cheong-Sun Lee, Suwon-si (KR); Dae-Hyun Sim, Seoul (KR)

(73) Assignee: Samsung Electronics Co., Ltd (KR)

( * ) Notice: Subject to any disclaimer, the term of this patent is extended or adjusted under 35 U.S.C. 154(b) by 1372 days.

(21) Appl. No.: 11/591,110

(22) Filed: Nov. 1, 2006

(65) Prior Publication Data

US 2007/0098187 A1    May 3, 2007

(30) Foreign Application Priority Data

Nov. 1, 2005 (KR) .................. 10-2005-0103906

(51) Int. Cl.
*H03G 5/00* (2006.01)
(52) U.S. Cl. ............ 381/103; 381/60; 381/79; 600/559
(58) Field of Classification Search ............ 381/58–60, 381/103, 77, 79, 98, 95, 96, 101, 102; 600/559
See application file for complete search history.

(56) References Cited

U.S. PATENT DOCUMENTS

| | | | | |
|---|---|---|---|---|
| 4,809,708 | A | * | 3/1989 | Geisler et al. ............... 600/559 |
| 5,651,371 | A | * | 7/1997 | Keefe ........................... 600/559 |
| 5,699,809 | A | * | 12/1997 | Combs et al. ............... 600/558 |
| 5,825,894 | A | | 10/1998 | Shennib |
| 5,919,143 | A | * | 7/1999 | Jenkins et al. ............... 600/549 |
| 7,190,795 | B2 | * | 3/2007 | Simon ............................ 381/60 |
| 7,194,100 | B2 | * | 3/2007 | Kuhnel et al. ............... 381/321 |
| 2003/0028385 | A1 | | 2/2003 | Christodoulou |
| 2005/0094822 | A1 | | 5/2005 | Swartz |

FOREIGN PATENT DOCUMENTS

| | | |
|---|---|---|
| DE | 41 28 172 | 3/1993 |
| EP | 1 073 314 | 1/2001 |
| KR | 1019990040058 | 6/1999 |
| KR | 100235170 | 9/1999 |

* cited by examiner

*Primary Examiner* — Vivian Chin
*Assistant Examiner* — Jason R Kurr
(74) *Attorney, Agent, or Firm* — The Farrell Law Firm, P.C.

(57) ABSTRACT

Disclosed is a method for reproducing a music file in a terminal equipped to reproduce the music file, the method including determining equalizing reproduction characteristics of the music file when reproduction of the music file is requested, determining and setting an output equalizer setting value of an audio signal, according to the equalizing reproduction characteristics and pre-measured individual hearing ability state information representing hearing ability characteristics of a user, and reproducing the music file so as to output the audio signal according to the output equalizer setting value.

11 Claims, 4 Drawing Sheets

METHOD AND APPARATUS FOR REPRODUCING MUSIC FILE

PRIORITY

This application claims the benefit under 35 U.S.C. 119(a) of an application entitled "Method And Apparatus For Reproducing Music File" filed in the Korean Intellectual Property Office on Nov. 1, 2005 and assigned Serial No. 2005-103906, the entire contents of which are incorporated herein by reference.

BACKGROUND OF THE INVENTION

1. Field of the Invention

The present invention relates to a terminal capable of reproducing a music file, and more particularly to a method and apparatus for reproducing a music file with an optimum level according to the hearing ability of the user.

2. Description of the Related Art

Recently, various types of terminals for providing a music file reproduction function have been developed. Such terminals range in type from various portable music file reproduction devices such as a CD player and an MP3 player, to a mobile communication terminal and a personal digital assistant (PDA). In addition, active research is taking place in order to provide high quality music reproduction. Generally, the music file reproduction terminals use a music file reproduction scheme which outputs an audio signal through fixed-frequency equalization. Even a music file production terminal having a separate frequency equalizing function includes a frequency equalizer, which can use frequency levels only within a specified frequency band or in three or five predetermined frequency bands among the entire audible frequency band. However, every person has varying hearing ability characteristics. Therefore, an audio signal undergoing fixed-frequency equalization cannot satisfy a plurality of unspecified users, and even a music file reproduction terminal including a simple equalizer cannot satisfy all users because the selectable frequency bands are fixed in the equalizer in advance. If a frequency equalizer capable of controlling a plurality of frequency band levels is included in a music file reproduction terminal in order to solve such a problem, the size of the frequency equalizer is enlarged, thereby degrading the portability of the music file reproduction terminal.

Therefore, it is necessary to develop a music file reproduction method and a terminal, which can reproduce and output an audio signal from a music file by accounting for the hearing ability characteristics of individuals.

SUMMARY OF THE INVENTION

Accordingly, the present invention has been made to solve the above-mentioned problems occurring in the prior art, and an object of the present invention is to provide a method and an apparatus for reproducing a music file, which can reproduce and output an audio signal from a music file according to the hearing ability characteristics of the users.

Another object of the present invention is to provide a method and an apparatus for reproducing a music file, which can satisfy users by providing a high quality music reproduction.

To accomplish this object, there is provided a method for reproducing a music file in a terminal which can reproduce the music file, the method including determining equalizing reproduction characteristics of the music file when reproduction of the music file is requested, determining and setting an output equalizer setting value of an audio signal, according to the equalizing reproduction Characteristics and pre-measured individual hearing ability state information representing hearing ability characteristics of a user, and reproducing the music file so as to output the audio signal according to the output equalizer setting value.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENT

Hereinafter, a preferred embodiment of the present invention will be described with reference to the accompanying drawings. In the following description, a detailed description of known functions and configurations incorporated herein will be omitted for the sake of clarity and conciseness.

Figure 1:
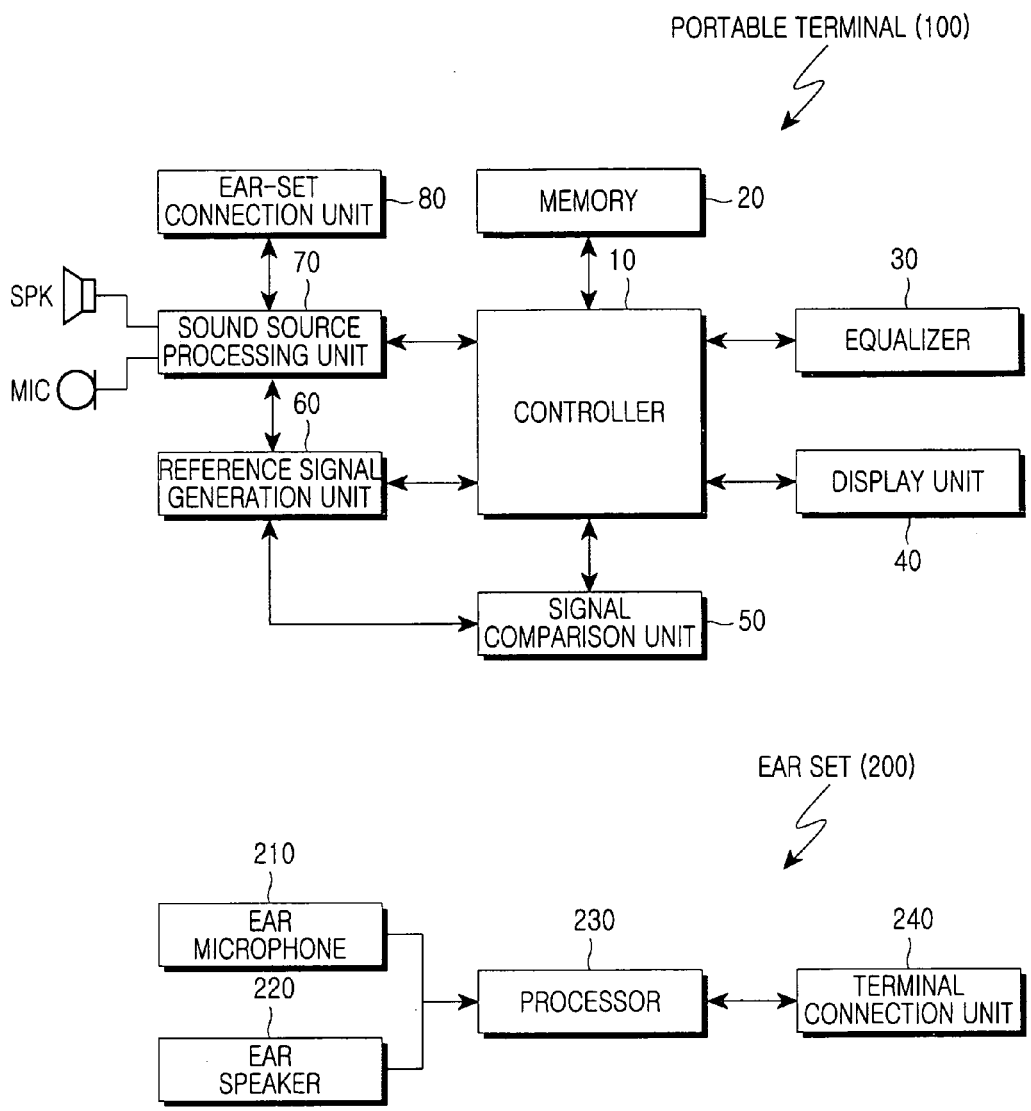
FIG. 1 is a block diagram illustrating the constructions of a music file reproduction terminal and an ear set according to the present invention.

FIG. 1 is a block diagram illustrating the constructions of a music file reproduction terminal and an ear set according to the present invention. A music file reproduction apparatus according to the present invention includes a music file reproduction terminal 100 and an ear set 200.

According to the present invention, when the user wears the ear set 200 on his/her ear and then inputs a request for individual hearing ability state measurement, the music file reproduction terminal 100 generates and transmits a basic audible frequency signal to the ear set 200 in response to the request. The ear set 200 outputs a received basic audible frequency signal, gathers signals reflected by the eardrum or inner wall of the ear by using a microphone 210, and transmits the gathered and measured reflection signals to the music file reproduction terminal 100. The music file reproduction terminal 100 generates an optimum reference audible frequency signal by comparing the received reflection signals with a standard reflection signal, and thereby measures an individual hearing ability state of the user. When reproducing a music file, the music file reproduction terminal 100 equalizes an audio signal of the music file according to the measured individual hearing ability state before outputting the music file.

Such a music file reproduction terminal 100 includes a controller 10, a memory 20, an equalizer 30, a display unit 40, a signal comparison unit 50, a reference signal generation unit 60, a sound source processing unit 70 and an ear-set connection unit 80. The ear set 200 includes an ear microphone 210, an ear speaker 220, a processor 230 and a terminal connection unit 240.

The controller 10 controls the entire operation of the music file reproduction terminal 100.

The memory 20 stores programs for the processing operation and control of the controller 10, reference and updatable storage data, and provides a working memory for the controller 10. In addition, the memory 20 stores basic audible frequency signal information, standard reflection signal information and individual hearing ability state information. The basic audible frequency signal information covers the entire audible frequency band, and represents a signal, the signal level of which is uniform for each frequency. The standard reflection signal information represents a signal, which is reflected by the eardrum or inner wall of an ear and is measured when the basic audible frequency signal information has been output to the ear of a person with a normal hearing ability.

The ear-set connection unit 80 represents a connection section required to communicate between the music file reproduction terminal 100 and the ear set 200. The ear-set connection unit 80 transmits an audio signal, which has been input from the sound source processing unit 70, to the ear set 200 connected to the ear-set connection unit 80, and outputs an audio signal received from the ear set 200 to the sound source processing unit 70. In addition, the ear-set connection unit 80 includes an access connector and a local-area wireless module such as a Bluetooth® module. The access connector is connected to a connection node of the ear set 200 so as to connect the ear set 200 and the music file reproduction terminal 100 by wire, and the local-area wireless module is used to wirelessly connect the ear set 200 and the music file reproduction terminal 100.

The sound source processing unit 70 processes an audio signal according to reproduction of a music file and outputs the processed audio signal to a speaker or the ear-set connection unit 80, under the control of the controller 10. Also, the sound source processing unit 70 processes an audio signal input from a microphone and outputs the processed audio signal to the controller 10. The sound source processing unit 70 appropriately processes a signal input from the reference signal generation unit 60 and outputs the processed signal to the ear-set connection unit 80 under the control of the controller 10, and outputs a measured reflection signal input from the ear-set connection unit 80 to the controller 10.

The reference signal generation unit 60 generates an audible frequency according to basic audible frequency signal information under the control of the controller 10, and outputs the generated audio frequency to the sound source processing unit 70. In addition, the reference signal generation unit 60 generates a reference audible frequency according to reference audible frequency information input from the signal comparison unit 50, and outputs the generated reference audible frequency to the sound source processing unit 70.

The signal comparison unit 50 compares a measured reflection signal, which has been input through the controller 10 from the sound source processing unit 70, with the standard reflection signal according to frequencies under the control of the controller 10, and determines whether a level difference in each frequency between the measured reflection signal and the standard reflection signal is within a tolerance range. When the level difference in a frequency between the two signals is outside of the tolerance range, the signal comparison unit 50 changes a relevant frequency level of the basic audible frequency signal by a preset level so as to determine a reference audible frequency, and outputs information about the determined reference audible frequency to the reference signal generation unit 60. When the level of a predetermined frequency of the measured reflection signal is less than the level of the corresponding frequency of the standard reflection signal, the signal comparison unit 50 increases the level of the predetermined frequency of the basic audible frequency signal by a preset level. In contrast, when the level of a predetermined frequency of the measured reflection signal is greater than the level of a corresponding frequency of the standard reflection signal, the signal comparison unit 50 decreases the level of the predetermined frequency of the basic audible frequency signal by a preset level.

Through such a procedure, a reference audible frequency (i.e. a first reference audible frequency) is determined, and the first reference audible frequency is output to the ear set 200. Thereafter, a measured reflection signal is also received and compared with the standard reflection signal, and depending on the result of the comparison, the first reference audible frequency is adjusted to generate a second reference audible frequency. When the level difference in each frequency between the measured reflection signal and the standard reflection signal is within the tolerance range through repetition of such a procedure, the signal comparison unit 50 outputs a last determined reference audible frequency to the controller 10, so as to be stored as the individual hearing ability state information of the user in the memory 20. The individual hearing ability state information corresponds to a signal having a signal level which, according to hearing ability characteristics of a user, is increased and decreased in frequency bands among the frequencies included in the basic audible frequency signal, in which the user has a dull sense of hearing and a keen sense of hearing, by the degrees of dullness and keenness, respectively. The individual hearing ability state information has different characteristics depending on each person, and may be influenced by external circumstances.

The equalizer 30 compares the reproduction characteristics of a music file to be reproduced with the individual hearing ability state information so as to determine a correction value, and sets an equalization value for an audio signal output of the music file reproduction terminal 100 according to the correction value. In other words, when it is necessary to emphasize a specific frequency band according to the reproduction characteristics of a music file to be reproduced, the level of the specific frequency of an output audio signal must be amplified by a predetermined level, and in this case, an amplification value is determined by considering the individual hearing ability state information. For example, the equalizer 30 may be constructed in such a manner that it sets frequency-by-frequency level values according to a reference audible frequency signal, which is determined by the individual hearing ability state information, as basic output equalizer setting values for an audio signal, and finally sets up an output equalizer by increasing or decreasing the equalizer setting values depending on the reproduction characteristics of a predetermined music file. According to the present invention, it is also possible for the controller 10 to arithmetically calculate an equalizer setting value according to the reproduction characteristics of a music file and the individual hearing ability state information, thereby finally setting up an output equalizer.

The ear microphone 210 and the ear speaker 220, which are included in the ear set 200, are constructed in the same unit. That is, according to the present invention, the ear microphone 210 must have a structure which can gather a sound reflected by the inner wall of a user's ear. Preferably, the ear microphone 210 is a condenser microphone.

The processor 230 outputs an audio signal input from the terminal connection unit 240 to the ear speaker 220, and outputs an audio signal input from the ear microphone 210 to the terminal connection unit 240. The ear set 200 may include a volume key for volume control, and may include a plurality of keys for generating key data to control the operation of the music file reproduction terminal 100.

The terminal connection unit 240 represents a connection section required to communicate between the music file reproduction terminal 100 and the ear set 200. The terminal connection unit 240 transmits an audio signal input from the processor 230 to the music file reproduction terminal 100, and outputs an audio signal received from the music file reproduction terminal 100 to the processor 230. In addition, the ear-set connection unit 80 includes a connection node and a local-area wireless module such as a Bluetooth® module. The connection node is connected to the access connector of the music file reproduction terminal 100 so as to connect the ear set 200 and the music file reproduction terminal 100 by wire, and the local-area wireless module is used to wirelessly connect the ear set 200 and the music file reproduction terminal.

The procedure for measuring the individual hearing ability state information of the user by using the music file reproduction terminal 100 and the ear set 200 according to the present invention will now be described with reference to FIGS. 2 to 4. Before the user inputs a request for an individual hearing ability state measurement to the music file reproduction terminal 100, it is necessary to wear a unit including the ear microphone 210 and ear speaker 220 of the ear set 200 on an ear of the user, as shown in FIG. 4. In this case, the unit of the ear set 200 is preferably in contact with as much of the ear as possible, and the unit of the ear set 200 may be an insertion-type earphone as shown in FIG. 4, which illustrates a construction for measuring individual hearing ability state information according to the present invention. Thereafter, when the user requests measurement of an individual hearing ability state through a key input or the like in step 301 of FIG. 2, the controller 10 proceeds to step 303.

Figure 2:
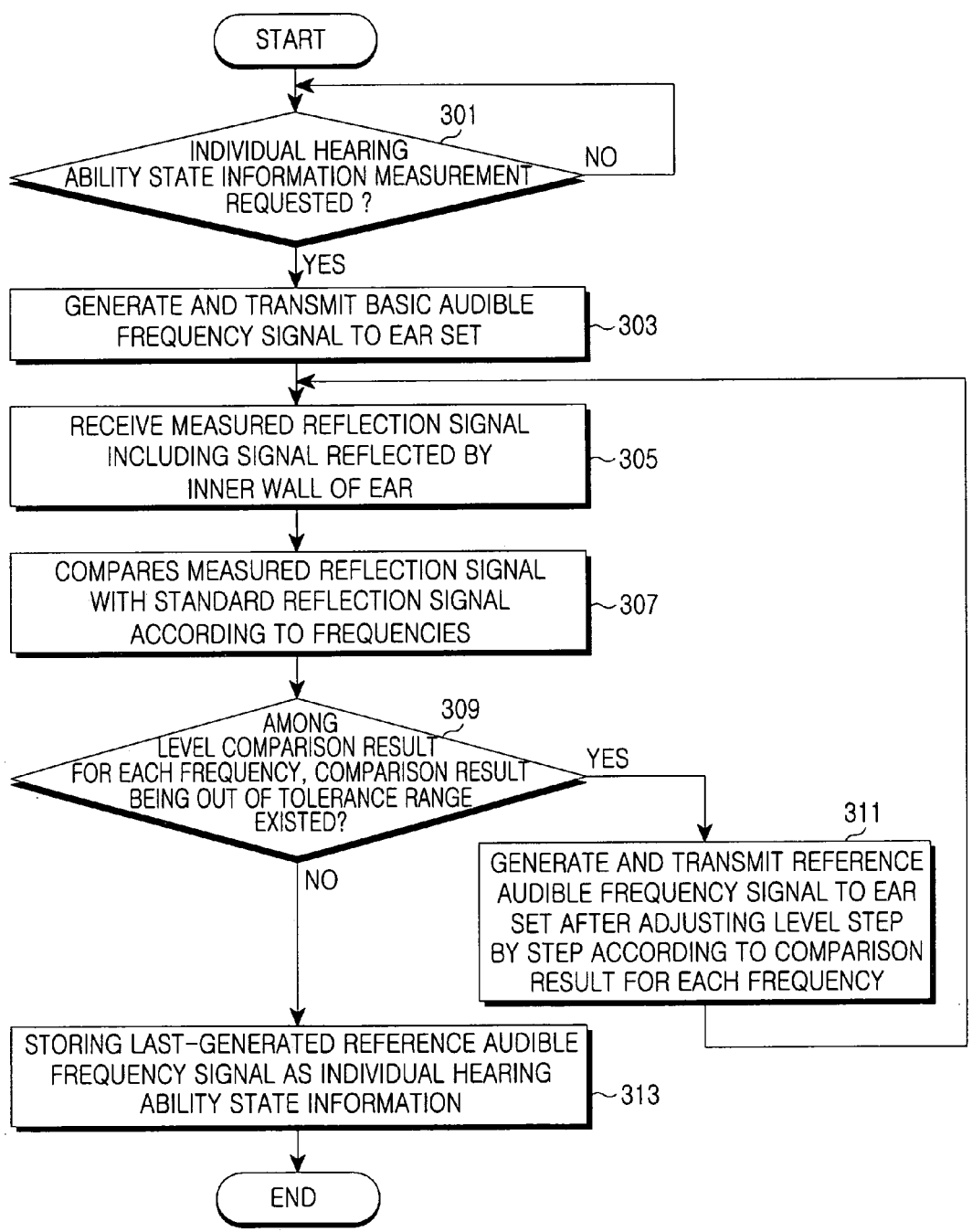
FIG. 2 is a flowchart illustrating the operation of the music file reproduction terminal to measure individual hearing ability state information according to the present invention.

FIG. 2 is a flowchart illustrating the operation of the music file reproduction terminal to measure individual hearing ability state information according to the present invention. In step 303, the controller 10 reproduces and transmits a basic audible frequency signal to the ear set 200, and then proceeds to step 305.

Then, the ear set 200 outputs the received basic audible frequency signal through the ear speaker 220. The output basic audible frequency signal is reflected by the eardrum or inner wall of the ear, as shown in FIG. 4, and reflected signals are gathered by the ear microphone 210 and are then output to the processor 230. The processor 230 transmits a measured reflection signal, which has been input as described above, through the terminal connection unit 240 to the music file reproduction terminal 100.

In step 305, the controller 10 receives the measured reflection signal, which includes signals reflected by the inner wall of the user's ear, from the ear set 200, and then proceeds to step 307. In step 307, the controller 10 compares the measured reflection signal with the standard reflection signal according to frequencies, and then proceeds to step 309. In step 309, the controller 10 determines whether there exists a comparison result representing that the level difference in a frequency between the two signals is outside of the tolerance range, among the comparison results for the difference in each frequency between the two signals. When it is determined in step 309 that there exists a comparison result representing that the level difference in a frequency between the two signals is outside of the tolerance range, the controller 10 proceeds to step 311, but when it is determined that there is no such comparison result, the controller 10 proceeds to step 313. In step 311, the controller 10 generates a reference audible frequency signal by adjusting a frequency level according to steps based on the comparison results for each frequency, transmits the generated reference audible frequency signal to the ear set 200, and returns to step 305; thereby repeating steps 305 to 309. When it is determined, as a result of comparing the signal levels of every frequency between a measured reflection signal and the standard reflection signal in step 309, that the level difference in every frequency between the two signals is within the tolerance range, the controller 10 stores a last generated reference audible frequency signal as individual hearing ability state information (step 313), and ends the procedure.

After the individual hearing ability state information has been measured and stored, when the user requests reproduction of a predetermined music file, the music file reproduction terminal 100 first determines the reproduction characteristics of the predetermined music file. Then, the music file reproduction terminal 100 determines and sets an equalizer setting value for an output audio signal according to the determined reproduction characteristics based on the individual hearing ability state information, and reproduces and outputs the predetermined music file.

Figure 3:
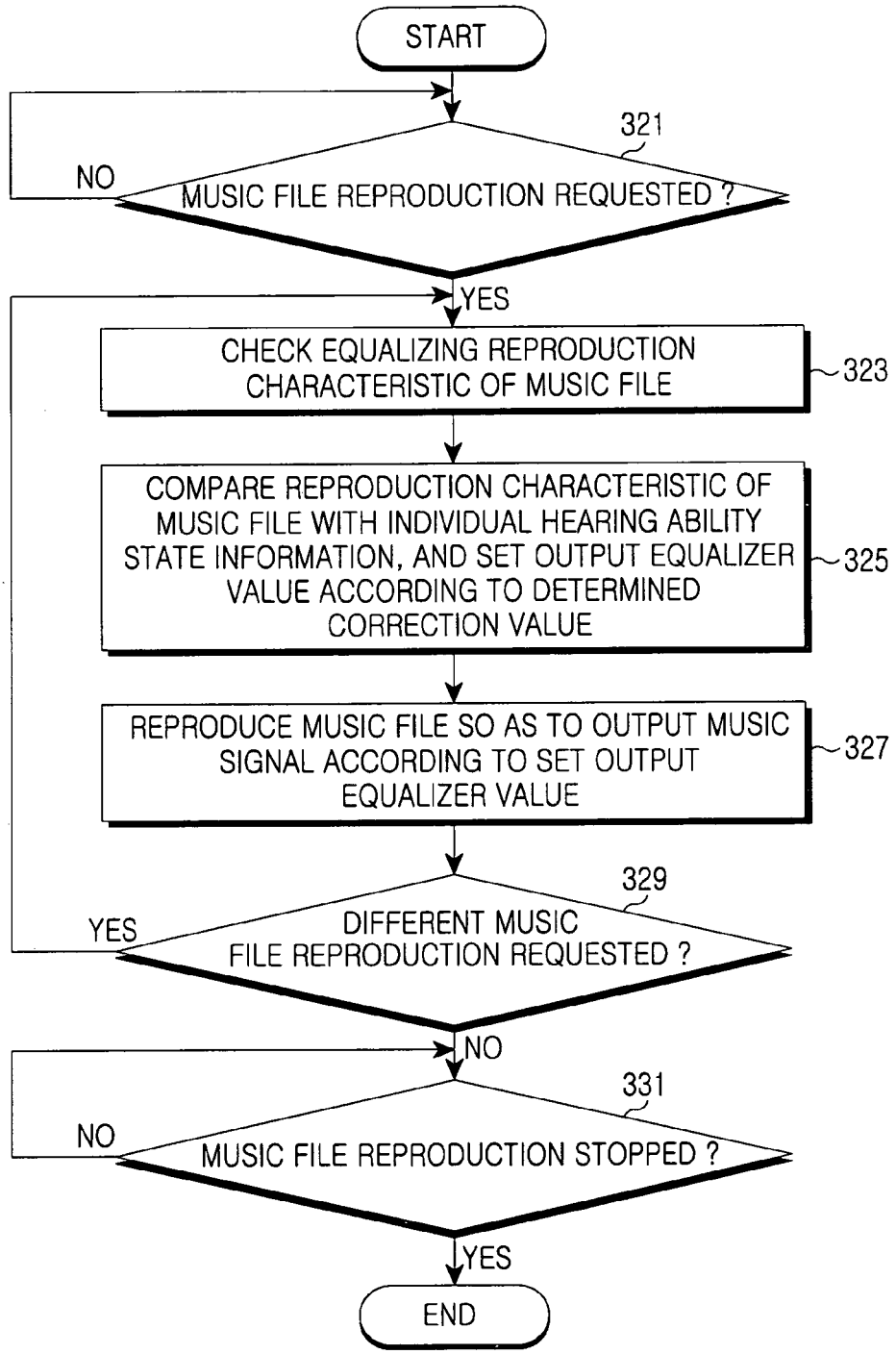
FIG. 3 is a flowchart illustrating the procedure for reproducing a music file based on individual hearing ability state information according to the present invention.
Figure 4:
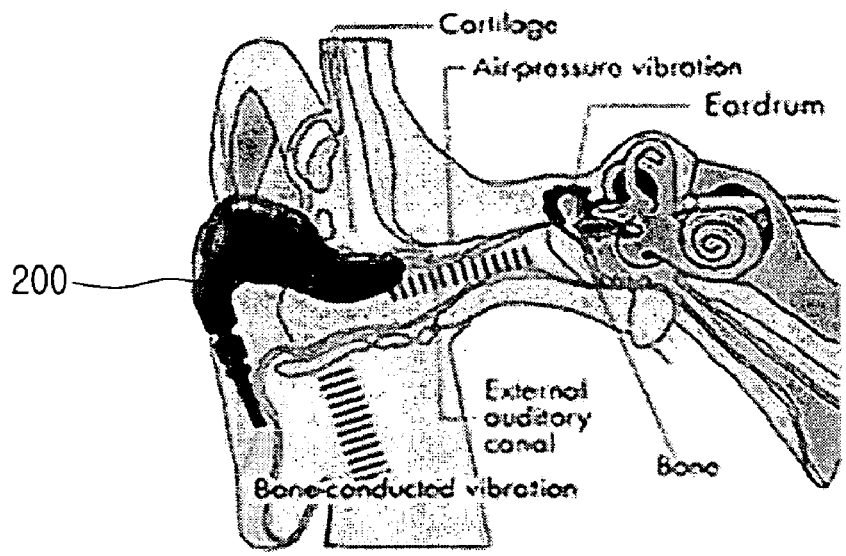
FIG. 4 is a view illustrating a construction for measuring individual hearing ability state information according to the present invention.

FIG. 3 is a flowchart illustrating the procedure for reproducing a music file based on individual hearing ability state information according to the present invention. When reproduction of a music file is requested by the user through a key input or the like in step 321, the controller 10 of the music file reproduction terminal 100 proceeds to step 323. In step 323, the controller 10 determines the reproduction characteristics of the music file, and then proceeds to step 325. In step 325, a correction value is determined by comparing the reproduction characteristics of the music file with individual hearing ability state information, and an output equalizer value is set according to the determined correction value. In step 327, the controller 10 outputs a music signal based on the reproduction characteristics of the music file and the set output equalizer value, and proceeds to step 329. In step 329, the controller 10 determines whether there exists a reproduction request for a different music file. When there exists a reproduction request for a different music file, the controller 10 proceeds to step 323, thereby repeating steps 323 to 329. Thereafter, in step 331, when receiving a reproduction stop request for a music file, the controller 10 stops reproducing the music file and ends its operation.

As described above, according to the present invention, individual hearing ability state information for each user is measured, and a final output equalizer setting value is set by determining the reproduction characteristics of a music file to be reproduced, so that it is possible to output an audio signal according the hearing ability characteristics of the user.

While the present invention has been shown and described with reference to certain preferred embodiments thereof, it will be understood by those skilled in the art that various changes in form and details may be made therein without departing from the spirit and scope of the invention as defined by the appended claims. For example, the music file reproduction terminal 100 may be a portable music file reproduction device, such as a mobile communication terminal, a personal digital assistant (PDA), a CD player, or an MP3 player, and may be any device capable of reproducing a music file, such as an audio device. That is, the music file reproduction terminal 100 includes all terminals capable of reproducing a music file, as well as portable terminals. Accordingly, the scope of the invention is not to be limited by the above embodiments but by the claims and the equivalents thereof.

What is claimed is:

1. A method for reproducing a music file in a terminal which can reproduce the music file, the method comprising the steps of:
   measuring individual hearing ability state information by transmitting a basic audible frequency signal to an ear set of a user and outputting a basic audible frequency signal including all audible frequency bands into an ear of the user;
   receiving a measured reflection signal, which has been reflected by an eardrum and inner wall of the user's ear according to the output of the basic audible frequency signal and has been gathered through an ear microphone of the ear set, from the ear set;
   determining whether a level difference in each frequency between the measured reflection signal and a pre-stored standard reflection signal is within a tolerance range, by comparing a level of the measured reflection signal with a level of a standard reflection signal according to frequencies;
   determining equalizing reproduction characteristics of the music file when reproduction of the music file is requested;
   determining and setting an output equalizer setting value of an audio signal, according to the equalizing reproduction characteristics and pre-measured individual hearing ability state information representing hearing ability characteristics of the user; and
   reproducing the music file so as to output the audio signal according to the output equalizer setting value.

2. A method for reproducing a music file in a terminal which can reproduce the music file, the method comprising the steps of:
   measuring individual hearing ability state information, which is determined according to hearing ability characteristics of a user, as requested by the user;
   determining equalizing reproduction characteristics of the music file when reproduction of the music file is requested;
   determining and setting an output equalizing setting value according to the equalizing reproduction characteristics based on the individual hearing ability state information of the user; and
   reproducing the music file so as to output an audio signal according to the output equalizer setting value,
   wherein measuring the individual hearing ability state information comprises:
   outputting a basic audible frequency signal including all audible frequency bands into an ear of the user through an ear speaker of an ear set, by transmitting the basic audible frequency signal to the ear set;
   receiving a measured reflection signal, which has been reflected by an eardrum and inner wall of the user's ear according to the output of the basic audible frequency signal and has been gathered through an ear microphone of the ear set, from the ear set;
   determining whether a level difference in each frequency between the measured reflection signal and a pre-stored standard reflection signal is within a tolerance range, by comparing a level of the measured reflection signal with a level of a standard reflection signal according to frequencies.

3. The method as claimed in claim 2, wherein the individual hearing ability state information step further comprises:
   generating a reference audible frequency signal by adjusting a level of a predetermined frequency of the basic audible frequency signal by a preset level value when it is determined that the level of the predetermined frequency of the basic audible frequency signal is outside of the tolerance range, and transmitting the reference audible frequency signal to the ear set, thereby outputting the reference audible frequency signal into the user's ear through the ear speaker of the ear set;
   receiving a measured reflection signal measured according to the output of the reference audible frequency signal from the ear set, comparing the measured reflection signal with the standard reflection signal, and repeating the steps of generating and outputting the reference audible frequency signal until a level difference in each frequency between the reference audible frequency signal and the standard reflection signal is within the tolerance range; and
   storing a last-output reference audible frequency signal as individual hearing ability state information when the level difference in each frequency between the two signals is within the tolerance range.

4. The method as claimed in claim 3, wherein, in the step of determining and setting an output equalizing setting value according to the equalizing reproduction characteristics based on the individual hearing ability state information of the user, a level value for each frequency based on the reference audible frequency signal, which has been determined as the individual hearing ability state information, is set as a basic output equalizer setting value for an audio signal, and an output equalizer is set up by increasing or decreasing the basic equalizer setting value according to the equalizing reproduction characteristics.

5. The method as claimed in claim 3, wherein, in the step of determining and setting an output equalizing setting value according to the equalizing reproduction characteristics based on the individual hearing ability state information of the user, an output equalizer is set up by arithmetically calculating an equalizer setting value according to the equalizing reproduction characteristics based on the individual hearing ability state information.

6. The method as claimed in claim 5, wherein the standard reflection signal has a reflection signal level demonstrated by a person having a normal hearing ability with respect to the basic audible frequency signal.

7. The method as claimed in claim 5, wherein the ear set includes the ear microphone and ear speaker, and is located within a selected distance from the user's ear when the unit is worn.

8. An apparatus for reproducing a music file, the apparatus comprising:
   a music file reproduction terminal for transmitting a basic audible frequency signal to an ear set by generating the basic audible frequency signal in response to an input of an individual hearing ability state information measurement request, generating a reference audible frequency signal appropriately adjusted from the basic audible frequency signal by comparing a measured reflection signal, which has been received according to an output of the basic audible frequency signal, with a standard reflection signal, storing the reference audible frequency signal as individual hearing ability state information of a user, and outputting an audio signal for reproduction of a music file by setting an output equalizing value for the audio signal according to the individual hearing ability state information and equalizing reproduction characteristics of the music file when the music file is reproduced;
   the ear set for outputting the basic audible frequency signal received from the music file reproduction terminal, gathering signals, which are reflected by an eardrum and an inner wall of a user's ear according to an output of the basic audible frequency signal, through an ear microphone, and transmitting a gathered and measured reflection signal to the music file reproduction terminal;

a controller for controlling an entire operation of the music file reproduction terminal; and a signal comparison unit for determining whether a difference in each frequency between the measured reflection signal and the standard reflection signal is within a preset tolerance range by comparing the two signals according to frequencies under control of the controller, determining a reference audible frequency signal by adjusting a level of a predetermined frequency of the basic audible frequency signal by a preset level when a difference in the predetermined frequency between the two signals is outside of the tolerance range, outputting information about the reference audible frequency to a reference signal generation unit, generating a new reference audible frequency signal by adjusting a current reference audible frequency signal by the preset level until the difference is within the tolerance range, and storing a last reference audible frequency signal as the individual hearing ability state information when the difference is within the tolerance range.

9. The apparatus as claimed in claim 8, wherein the music file reproduction terminal comprises:

a memory for storing basic audible frequency signal information and standard reflection signal information;

the reference signal generation unit for generating an audible frequency according to reference audible frequency signal information under control of the controller, outputting the audible frequency to a sound source processing unit, and generating a reference audible frequency according to reference audible frequency information input from the signal comparison unit;

an equalizer for setting an output equalizer setting value of an audio signal for the music file reproduction terminal based on a correction value, which is determined by comparing reproduction characteristics of a music file to be reproduced with the individual hearing ability state information, when the music file is reproduced under control of the controller; and an ear-set connection unit connected to the ear set so as to transmit the basic and reference audible frequency signals input from the reference signal generation unit to the ear set, and so as to output a measured reflection signal received from the ear set to the signal comparison unit.

10. The apparatus as claimed in claim 9, wherein the ear set includes the ear microphone and ear speaker, is constructed such that it is located within a selected distance from the user's ear when the unit is worn, and the ear set includes a terminal connection unit to be connected to the ear-set connection unit.

11. The apparatus as claimed in claim 8, wherein the individual hearing ability state information corresponds to a signal having a signal level which, according to hearing ability characteristics of a user, is increased and decreased in frequency bands among the frequencies included in the basic audible frequency signal, in which the user has a dull sense of hearing and a keen sense of hearing, by the respective degrees of dullness and keenness.

\* \* \* \* \*